(12) United States Patent
Whelan

(10) Patent No.: US 12,213,691 B2
(45) Date of Patent: Feb. 4, 2025

(54) DUAL CHANNEL THROMBECTOMY DEVICE

(71) Applicant: Neuravi Limited, Galway (IE)

(72) Inventor: Stephen Whelan, Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 18/218,230

(22) Filed: Jul. 5, 2023

(65) Prior Publication Data

US 2023/0355258 A1 Nov. 9, 2023

Related U.S. Application Data

(62) Division of application No. 16/946,362, filed on Jun. 18, 2020, now Pat. No. 11,737,771.

(51) Int. Cl.
| | | |
|---|---|---|
| A61B 17/221 | (2006.01) | |
| A61B 17/00 | (2006.01) | |
| A61B 17/22 | (2006.01) | |
| A61B 90/00 | (2016.01) | |

(52) U.S. Cl.
CPC .. *A61B 17/221* (2013.01); *A61B 2017/00867* (2013.01); *A61B 2017/22079* (2013.01); *A61B 2090/3966* (2016.02)

(58) Field of Classification Search
CPC ........ A61B 17/221; A61B 2017/22079; A61B 2090/3966
USPC ....................................................... 606/200
See application file for complete search history.

(56) References Cited

U.S. PATENT DOCUMENTS

| | | |
|---|---|---|
| 4,455,717 A | 6/1984 | Gray |
| 4,611,594 A | 9/1986 | Grayhack et al. |
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)

*Primary Examiner* — Kankindi Rwego

(74) *Attorney, Agent, or Firm* — Troutman Pepper Hamilton Sanders LLP

(57) ABSTRACT

A method for removing a clot from a vessel involves the use of a device that can have dual layers where an inner expandable member runs within an outer expandable member. The inner expandable member can be divided into one or more sections, with a proximal section having a clot pinching structure configured to pinch the clot between the pinching structure and an outer catheter. A distal flow channel section of the inner member can be configured to create a flow channel through the clot to restore blood to the downstream vasculature. The struts of the outer expandable member can form closed cells that are not fully circumferential in a proximal portion to allow a clot to pass inside and engage the pinching structure, and fully circumferential in a distal portion to scaffold the vessel for dislodging the clot. A protective element at the distal end of the device can prevent the escape of clot fragments.

19 Claims, 7 Drawing Sheets

(56) References Cited

U.S. PATENT DOCUMENTS

| | | |
|---|---|---|
| 5,011,488 A | 4/1991 | Ginsburg |
| 5,084,065 A | 1/1992 | MacGregor et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,174,329 B1 | 1/2001 | Callol et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,537,294 B1 | 3/2003 | Boyle et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |

(56) References Cited

U.S. PATENT DOCUMENTS

| | | |
|---|---|---|
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |

(56) References Cited

U.S. PATENT DOCUMENTS

| | | |
|---|---|---|
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,439,418 B2 | 9/2022 | O'Malley |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavlovic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |

(56) References Cited

U.S. PATENT DOCUMENTS

| | | |
|---|---|---|
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0069520 A1 | 4/2003 | Skujins et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0044399 A1 | 3/2004 | Ventura |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224176 A1 | 10/2006 | Fung et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0135826 A1 | 6/2007 | Zaver et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0173921 A1 | 7/2007 | Wholey et al. |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |

(56) References Cited

U.S. PATENT DOCUMENTS

| | | |
|---|---|---|
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0296274 A1 | 12/2008 | Bialas et al. |
| 2008/0312681 A1 | 12/2008 | Ansel et al. |
| 2009/0005853 A1 | 1/2009 | Osman |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0022572 A1 | 1/2012 | Braun et al. |
| 2012/0041449 A1 | 2/2012 | Eckhouse et al. |
| 2012/0041469 A1 | 2/2012 | Fischell et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0325107 A1 | 12/2013 | Wu |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |

(56) References Cited

U.S. PATENT DOCUMENTS

| | | |
|---|---|---|
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |

(56) References Cited

FOREIGN PATENT DOCUMENTS

| | | |
|---|---|---|
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3669802 A1 | 12/2019 |
| EP | 3593742 A1 | 1/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| JP | 2019-536552 A | 12/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

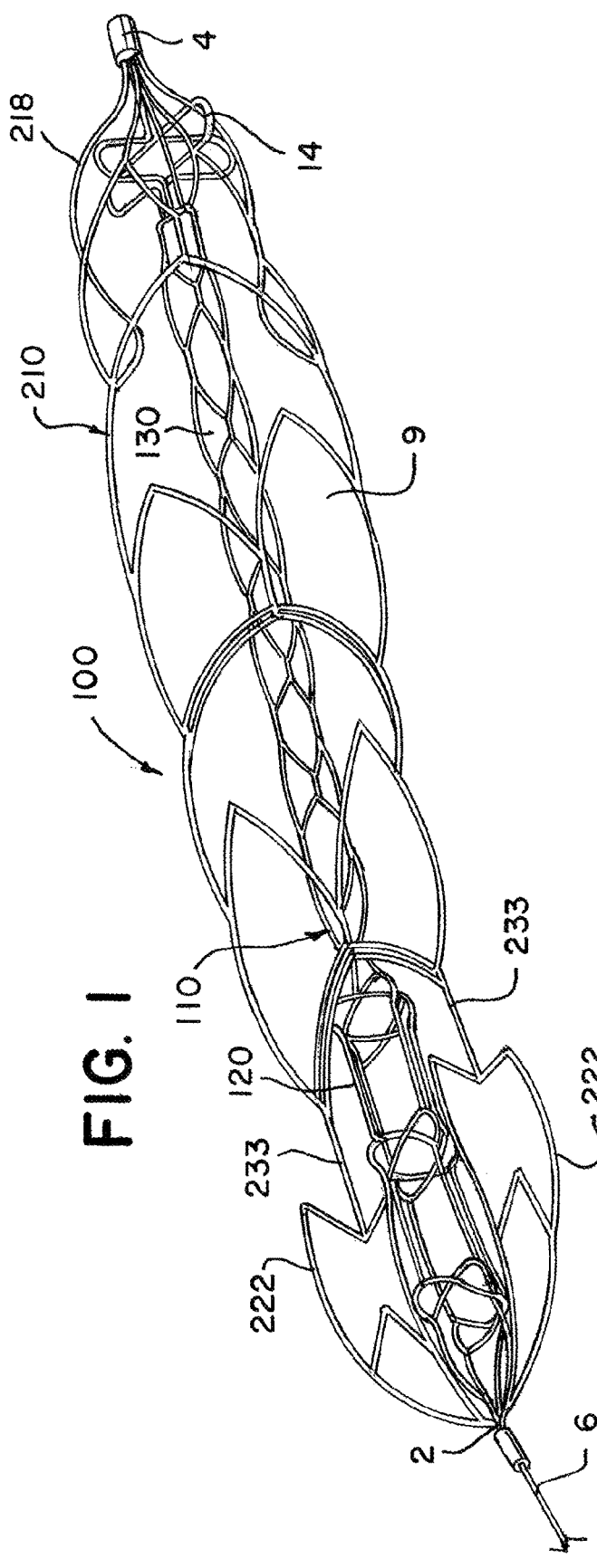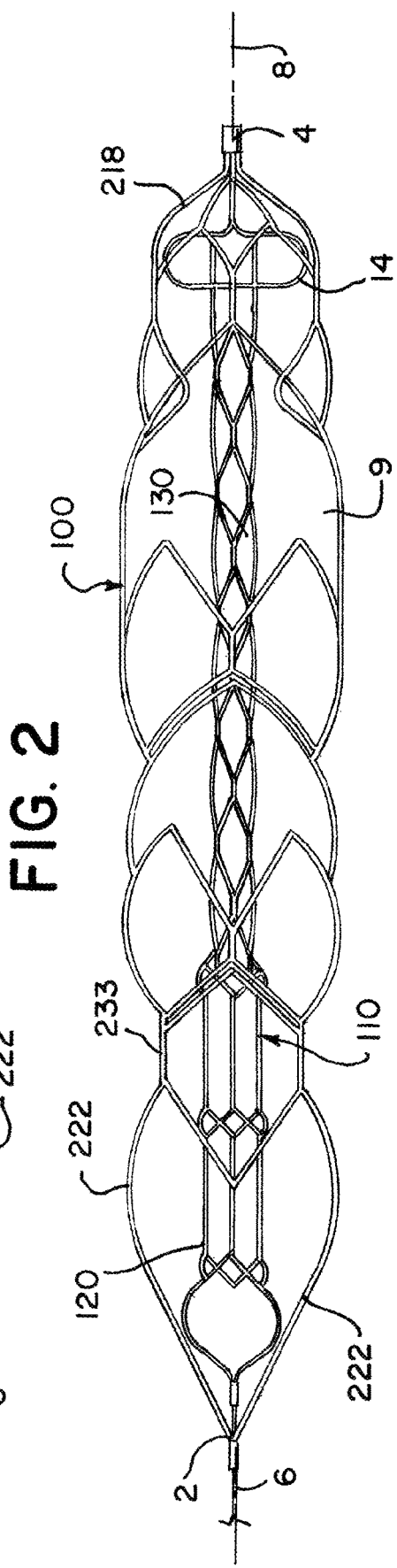

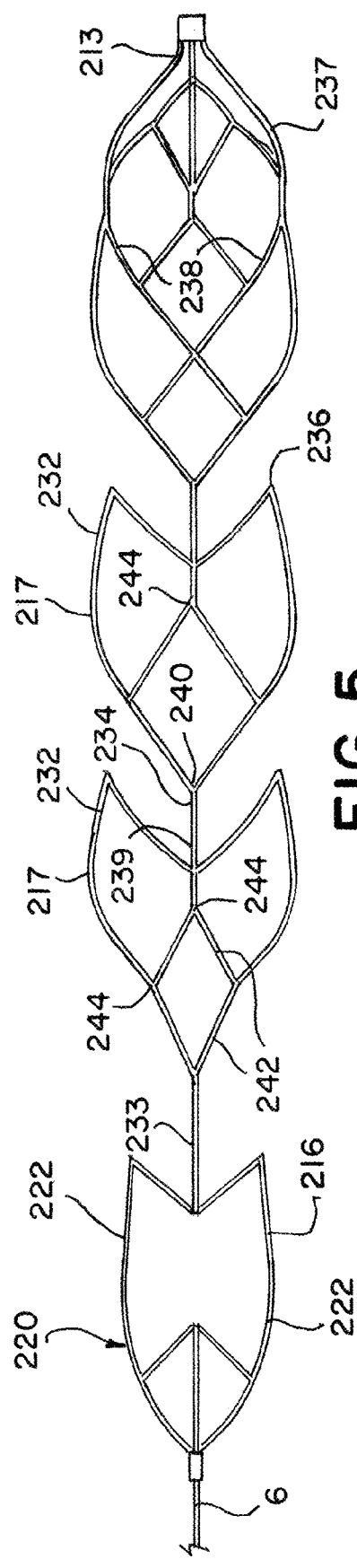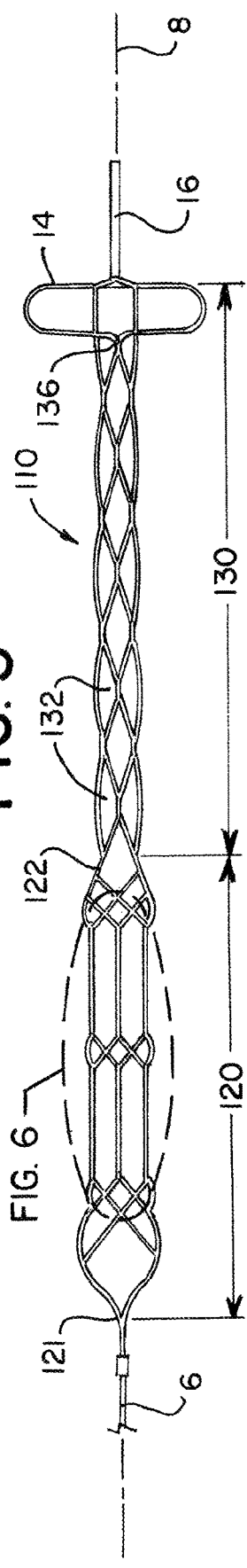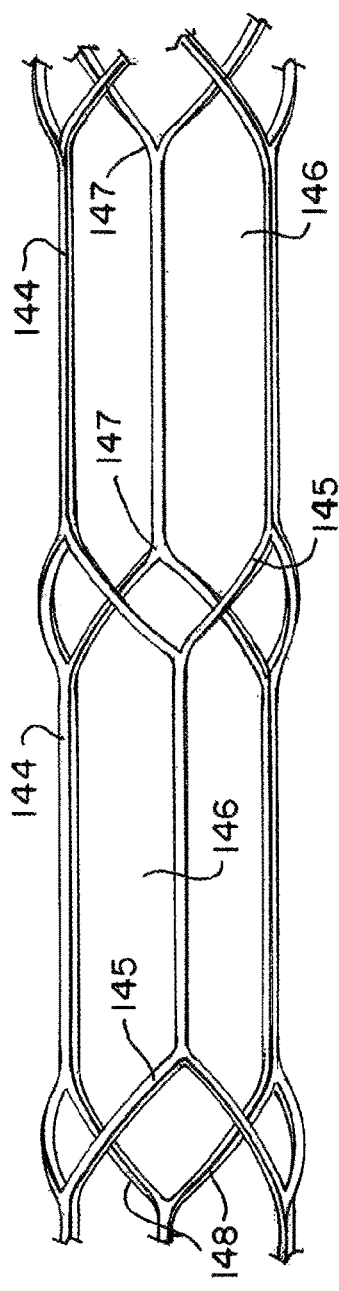

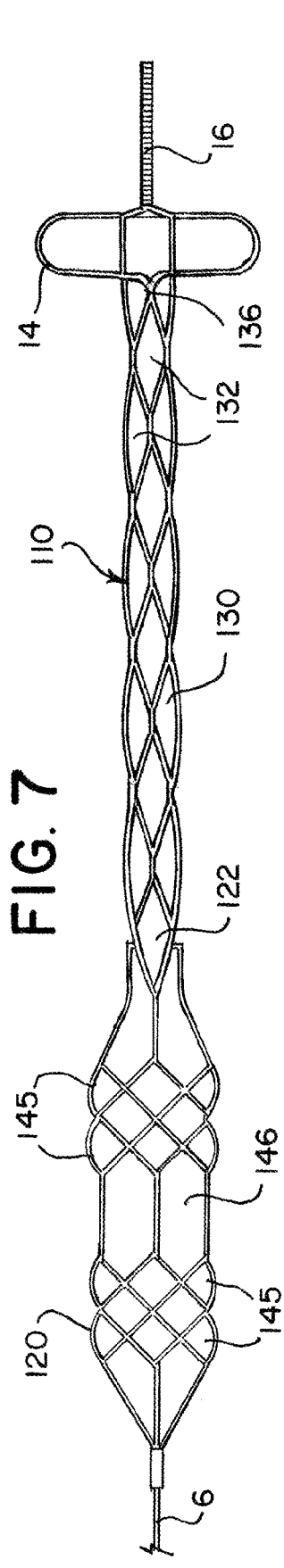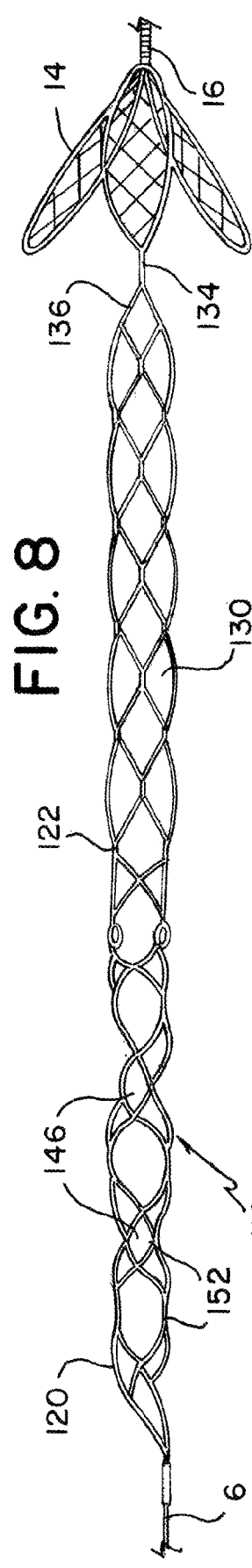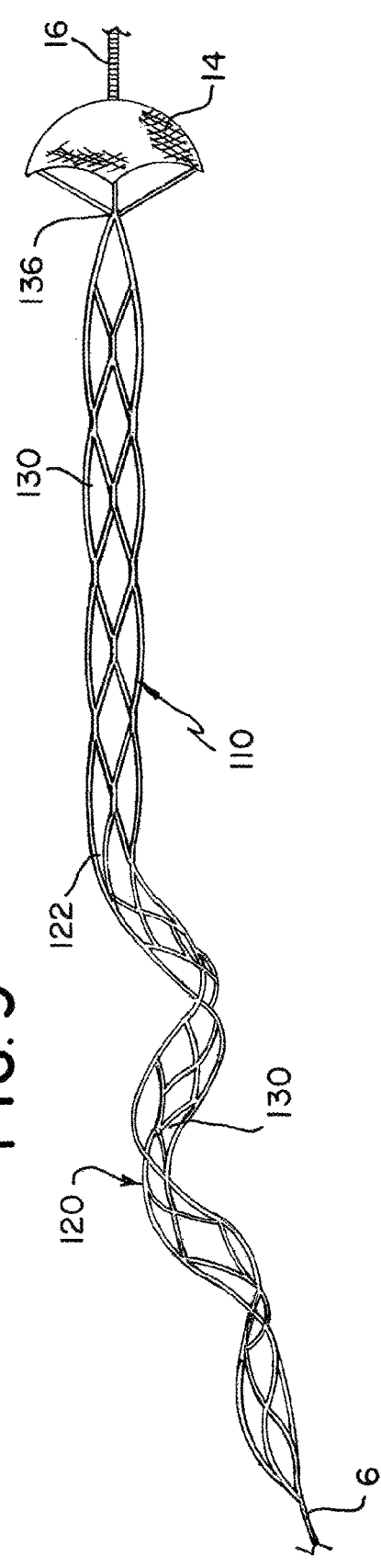

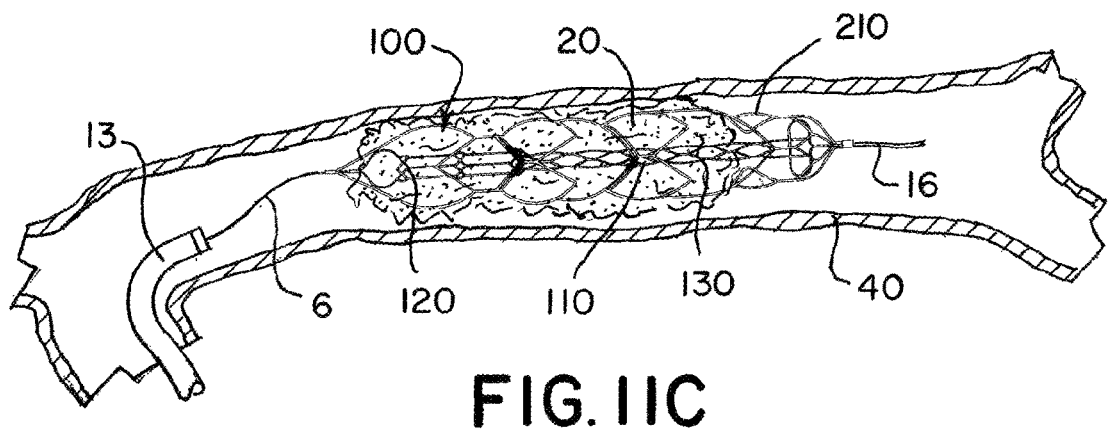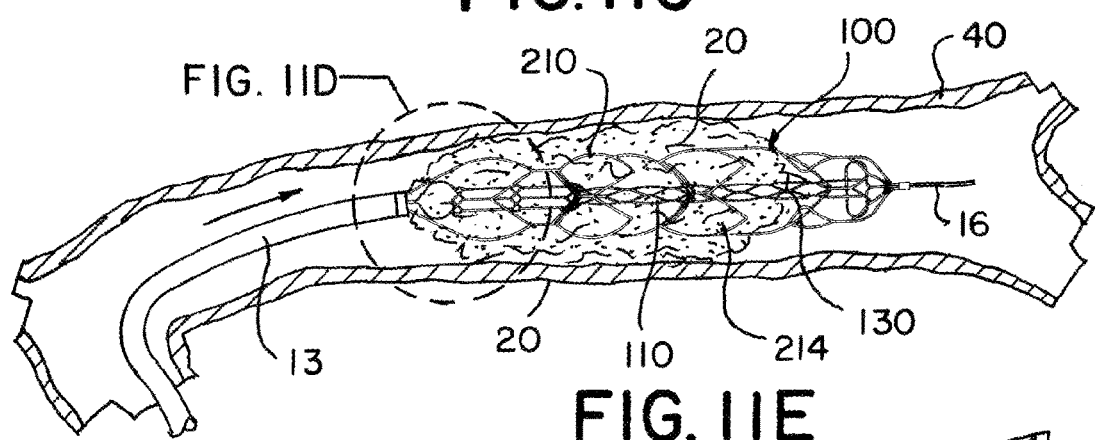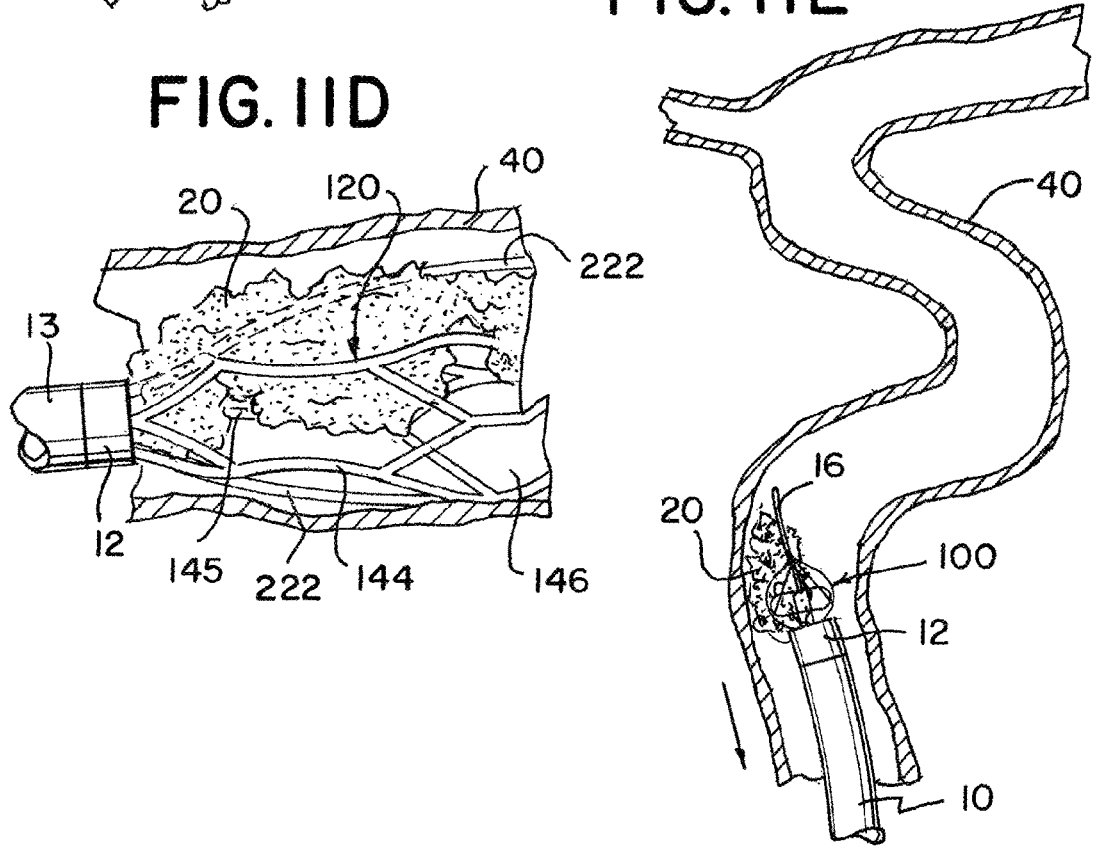

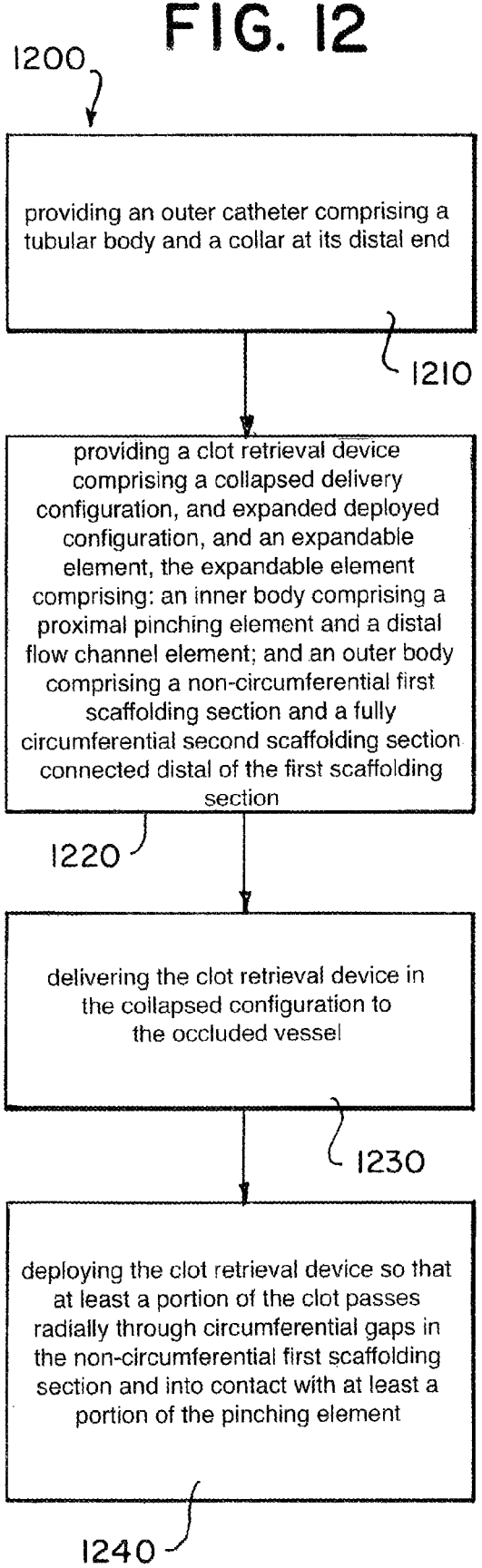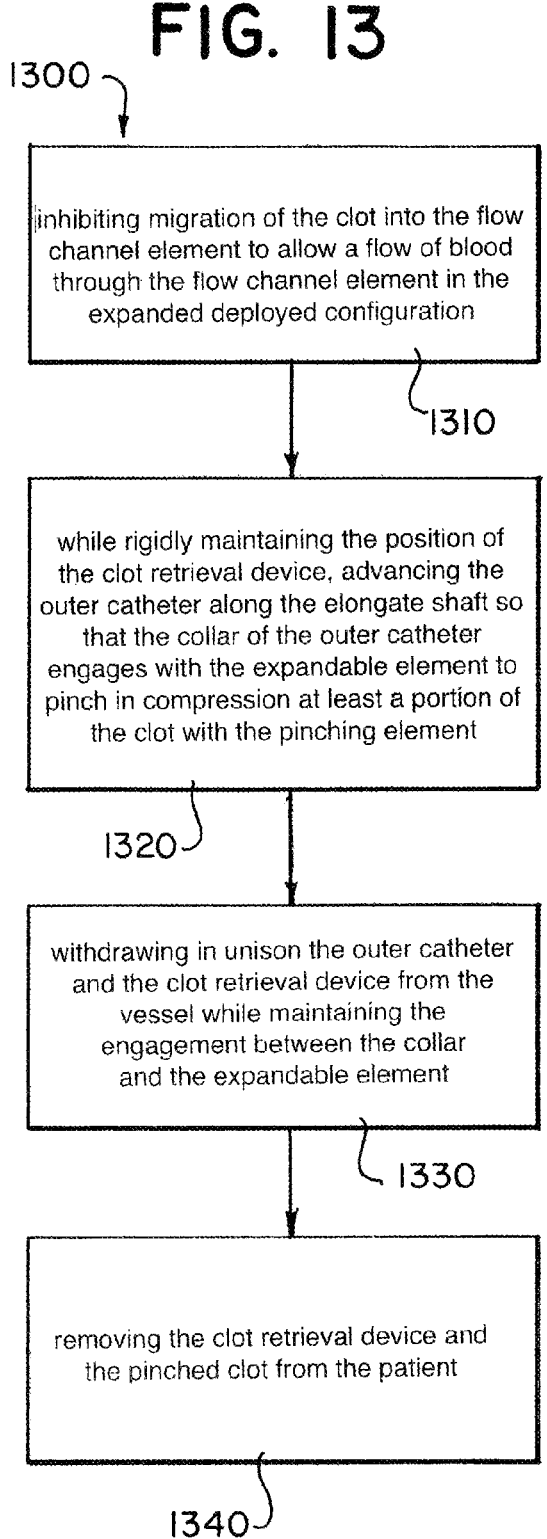

DUAL CHANNEL THROMBECTOMY DEVICE

CROSS REFERENCE TO RELATED APPLICATION

The present application is a divisional application of U.S. patent application Ser. No. 16/946,362 filed Jun. 18, 2020. The entire contents of which are hereby incorporated by reference.

FIELD OF THE INVENTION

The present disclosure generally relates to devices and methods for removing acute blockages from blood vessels during intravascular medical treatments. More specifically, the present disclosure relates to a clot retrieval device for removing a clot from a blood vessel.

BACKGROUND

This disclosure relates to devices and methods of removing acute blockages from blood vessels. Acute obstructions may include a clot, misplaced devices, migrated devices, large emboli, and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus, and this mechanism is common in the formation of coronary blockages. The devices and methods herein are particularly suited to removing clot from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which clot is causing an occlusion.

There are a number of access challenges that can make it difficult to deliver devices to a target site. In cases where access involves navigating the aortic arch (such as coronary or cerebral blockages) the configuration of the arch in some patients makes it difficult to position a guide catheter. The tortuosity challenge is even more severe in the arteries approaching the brain. It is not unusual at the distal end of the internal carotid artery that the device will have to navigate a vessel segment with several extreme bends in quick succession over only a few centimeters of travel. In the case of pulmonary embolisms, access may be gained through the venous system and then through the right atrium and ventricle of the heart. The right ventricular outflow tract and pulmonary arteries are delicate vessels that can easily be damaged by inflexible or high-profile devices. For these reasons it is desirable that a clot retrieval device be compatible with as low profile and flexible access and support catheters as possible.

The vasculature in the area in which the clot may be lodged is often fragile and delicate. For example, neurovascular vessels are more fragile than similarly sized vessels in other parts of the body and are located in a soft tissue bed. Excessive tensile forces applied on these vessels can result in perforations and hemorrhage. Pulmonary vessels are larger than those of the cerebral vasculature, but are also delicate in nature, particularly more distal vessels.

Stent-like clot retrieval devices are being increasingly used to remove a clot from cerebral vessels of acute stroke patients. These devices often rely on a pinning mechanism to grab the clot by trapping it between the self-expanding stent-like body and the vessel wall. This approach has a number of disadvantages.

A stent-like clot retriever depends on its outward radial force to retain its grip on the clot. This compressive force will tend to dehydrate the clot, which in turn can increase its coefficient of friction, making it more difficult to dislodge and remove from the vessel. If the radial force is too low the stent-like clot retriever will lose its grip on the clot, but if the radial force is too high the stent-like clot retriever may damage the vessel wall and require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle clot types in all thrombectomy situations. Pinning the clot between the stent-like clot retriever and the vessel wall also results in high shear forces against the side of the clot as it is removed, potentially releasing fragments of the clot. If these fragments are not retained by the device, they may be released leading to further blockages in the distal vasculature.

Certain conventional stent-like clot retriever designs also do not retain their expanded shape very well when placed in tension in vessel bends, due to the manner in which their strut elements are connected to one another which results in the struts being placed in tension during retraction. This tension is due to friction between the device and the blood vessel and is increased if an additional load is applied load such as the resistance provided by a clot. This can result in a loss of grip on the clot as the stent-like clot retriever is withdrawn proximally around a bend in a tortuous vessel, with the potential for the captured clot to escape. In a bend, the struts on the outside of the bend are placed in higher tension than those on the inside. In order to attain the lowest possible energy state, the outside surface of the clot retrieval device moves towards the inside surface of the bend, which reduces the tension in the struts, but also reduces the expanded diameter of the device.

Furthermore, when attempting to remove long clots, a conventional device that is shorter than the clot is unlikely to be able to restore flow through the occluded area upon deployment. As a result, the pressure gradient across the clot remains a significant impediment to its removal. Simply making such a device longer would likely render it difficult to track through tortuous anatomies and can be traumatic to the vasculature, taking more force to withdraw and potentially getting the device stuck, requiring surgery to remove.

In seeking procedural efficiency, devices with multiple bodies have also been used. Such devices can have an outer body capable of scaffolding a target vessel and an inner body for embedding and capturing a clot. These devices can perform well in engaging with and dislodging a clot but having a larger and often stiffer network of struts can potentially make it more difficult to retract the device and partially or fully re-sheath it within an outer catheter. Compression of the members of the outer body during this process can possibly interfere with or even loosen the grip of the inner body on a captured clot, especially for longer clots or in situations where grip is maintained between through a pinching action with the device and the distal tip of the outer catheter. The larger expanded shape of the outer body can result in the outer body struts impinging on or deflecting those of the inner body as the device is partially or fully collapsed during retraction.

The effectiveness of a given device is also important as, for many reasons, it is often necessary for a physician to make multiple passes in order to fully remove an obstruction Each time a clot retrieval device is withdrawn the access to the target site is lost. Thus, it can be necessary to re-advance a guidewire and microcatheter to access and re-cross the clot, and then remove the guidewire and advance the clot retrieval device through the microcatheter. Navigating the guidewire and microcatheter to the clot can take a considerable amount of time especially if the vessels are tortuous. The additional time and device manipulation add to the risks of complication to which the patient is exposed, highlighting the importance of effective and efficient devices.

The challenges described above need to be overcome for any device to provide a high level of success in removing a clot, restoring flow, and facilitating good patient outcomes. The present designs are aimed at providing an improved clot retrieval device to address the above-stated deficiencies.

SUMMARY

The designs herein can be for a clot retrieval device for removing clot from a body vessel. The device can have a framework of struts forming an elongate inner body with a proximal end, a distal end, and a longitudinal axis. The elongate inner body can be divided into one or more sections extending distally from a proximal shaft used to manipulate the device. A proximal section can have a clot pinching structure with a collapsed delivery configuration when constrained within an outer catheter, an expanded clot engaging configuration when deployed at a target site, and a clot pinching configuration where the pinching structure is at least partially constrained. As the device transitions from the engaging deployed configuration, the clot pinching structure can be configured to pinch and grasp the clot when in the clot pinching configuration.

The clot pinching structure can take a variety of forms, such as a flat pattern arranged in an undulating or spiral fashion. In one example, the pinching structure contains an array of adjacent segments. The segments can be sections of low strut density bordered by rings of higher density, or otherwise vary in shape at different longitudinal positions such that the radial force extorted in a clot by at least two adjacent segments differs from each other. In another example, the pinching structure can have a series of clot-receiving cells. The cells can consist of one or more flexible struts extending between crowns such that the cells are capable of constricting portions of a clot in the cells when the struts are in compression. These patterns allows a microcatheter or outer catheter to be advanced over the proximal end of the pinching structure in order to compress and grip a clot between the tip of the catheter and at least a portion of the struts of the pinching structure as the device is transitioned from the expanded deployed configuration to the partially-constrained clot pinching configuration.

A more distal section of the elongate inner body of the device can be a porous inner channel which can be fixedly connected to the distal end of the clot pinching structure. The inner channel can include a tubular main body composed of a plurality of struts defining inner body closed cells around the longitudinal axis. The cells and struts can be designed to penetrate the clot and exert a radial force to create a lumen through the clot and restore flow on deployment to a radially expanded configuration. The cells can also allow portions of the clot to escape compression by displacing through the cell openings, thereby reducing the radial force exerted on the vessel walls to minimize vessel trauma and reduce tensile disturbance of the distal vascular bed.

The device can have dual expandable members whereby the properties of the inner and outer members may be tailored independently of each other. In one example, an outer cage is supplied with the inner elongate body. The outer cage can be coaxial with the inner elongate member or can be radially offset. The outer cage can be expandable to a greater extent than the inner elongate body and configured to appose with and support the walls of a target vessel. The inner elongate body can be arranged substantially within the lumen of the outer cage. The difference in radial expansion between the inner body and outer cage can define a reception space between the two into which a clot can be received.

Similar to the inner elongate member, the outer cage can also have one or more sections. The cage can have a proximal first scaffolding segment with a framework of struts forming one or more proximal expandable bodies arranged longitudinally. The proximal expandable bodies can be made of non-circumferential closed cells forming one or more support arms spaced around the longitudinal axis so that large circumferential gaps exist between adjacent arms. For example, the first scaffolding segment of the outer cage can have two support arms diametrically opposed and spaced 180 degrees apart.

The outer cage can also have a distal second scaffolding segment with a framework of struts forming one or more distal expandable bodies arranged longitudinally. Similar to the first scaffolding segment, the second scaffolding segment can have a network of closed cells around the longitudinal axis. The cells of the distal expandable bodies of the second scaffolding segment can be fully circumferential so as to support the vessel at all clocking positions. The distal section of the elongate inner body, the porous inner channel, can be disposed within the lumen of the second scaffolding segment.

The closed cells of the first and second scaffolding segments of the outer cage can be larger than the cells of the inner body. As a result, the outer cage can be configured to be expanded within an occlusive clot in a blood vessel so that the cage allows the clot to migrate into the reception space within as the cage expands.

For increased device flexibility, the expandable bodies of the first and second scaffolding segments can be hingedly connected to each other so they can flex independently as the device is advanced or retracted through bends in the vasculature. Additionally, the cells of each expandable body of the first and second scaffolding segment can have struts forming at least one distal apex free from connection to an adjacent closed cell.

In another example, the clot retrieval device can have a dual layer setup with an inner elongate body disposed within a porous outer body. The inner elongate body can have a proximal clot engaging element having a constrained delivery configuration, an expanded clot engaging deployed configuration, and an at least partially constrained clot pinching configuration. Distal to the clot engaging element can be a tubular inner channel having a constrained delivery configuration and an expanded deployed configuration. When expanded, the tubular inner channel can utilize radial force to restore the flow of blood in an occluded vessel.

The clot engaging element can have a framework of struts configured to exert an outward radial force on a clot when expanded to the deployed configuration. The outward force can vary in amplitude along the length of the clot engaging element. In one case, the radial force follows a generally sinusoidal waveform pattern. The amplitude of the waveform pattern can be generally equal across peaks, or it can be different at the proximal or distal end for a firmer grip on portions of the clot. The amplitude of the peaks, for example, can decrease along the length of the clot engagement element so that it is higher at the proximal end and lower at the distal end.

The device can also have a longitudinal axis extending centrally through the proximal clot engaging element and distal tubular inner channel. The struts of the clot engaging element can be a flat pattern or planar so that when deployed to an expanded state the pattern aligns with or around the axis. In one example, the struts of the element can form a planar pattern that is twisted around the axis in a spiral or helical shape. In a separate example, the struts can form a plurality of adjacent segments with regions of high and low strut density, or longitudinal asymmetry such that the radial force exerted by two adjacent segments is different from each other to maintain better grip on a clot. In an additional case, adjacent struts of the clot engaging element can have bends or twists in the same or different direction to change the radial force so that a captured clot is compressed and pinched when the clot engaging element is moved to the clot pinching configuration.

Disposed around the inner elongate body in the dual layer device setup can be porous outer body with a non-circumferential proximal segment and a fully circumferential distal segment connected to the proximal segment. The outer body can be designed so that it expands to a radial extent greater than the radial expansion of the inner elongate body when the device is deployed from a delivery catheter. When folded inside the catheter, the outer body can have a radial size equal to or greater than that of the inner body.

The proximal segment and the distal segment of the porous outer body can each have one or more expandable bodies. The expandable bodies can each have a plurality of struts forming closed cells. The cells are generally larger than, for example, cells of the inner elongate body so that the expandable outer body can exert radial force on a clot and the target vessel while providing scaffolding that will not obstruct a clot from passing through and being captured by the inner body. Each expandable body of the proximal and distal segments can have struts join together in at least one distal apex that is free from connection with another adjacent closed cell, enhancing flexibility by allowing each body to flex and react to localized forces independently. Other portions of the expandable bodies can have regions of convergence where struts intersect with intermediate coupling struts or connecting arms joining adjacent bodies.

The embolization risk during clot retrieval with the device can be reduced by providing a distal fragment protection element appended to one or both of the inner elongate member or the outer cage. The protection element can consist of a net or scaffolding zone across the vessel lumen towards the distal end of the device. The element can be three dimensional in that it has depth as well as surface area. In other cases, fibers or fine wires can be utilized to provide added scaffolding in the element with minimal impact on device profile or deliverability. Combining a fragment protection element with the scaffolding of both the inner and outer members provides a more effective filter than utilizing one member alone In one example, the distal portion of the inner elongate body can have a plurality of struts which are configured as a fragment protection element in a volumetric pattern around the longitudinal axis. The distal portion of the inner elongate body can also have a bulged or flared framework of struts.

In an alternative example, the fragment protection element can be connected to or be a part of the distal end portion of the outer cage or member. The end of the outer cage can also taper through a series of distal crown struts. The crown struts of the outer member can be configured in a generally conical shape so that the outer member necks down distally as a natural barrier around the protection element. The struts can also cross over circumferentially to occupy more cross-sectional area or have strands in a mesh or braid for increased coverage.

A method for using the clot retrieval device to extract an occlusive clot from a vessel can include the step of providing an outer catheter having a tubular body and a collar at its distal end. Also provided can be a clot retrieval device with an elongate shaft mated to an expandable element capable of transitioning from a collapsed delivery configuration to an expanded deployed configuration. The clot retrieval device can have an inner body with a proximal clot pinching element connected to a more distal flow channel element. Arranged around the inner body can be an outer body with a non-circumferential first scaffolding section joined to a fully circumferential second scaffolding section. The second scaffolding section can have a pivoting or hinge-like connection to the first scaffolding section to allow the device to conform to sharp bends in the vasculature.

The method can involve delivering the clot retrieval device to the target occlusion in the collapsed configuration, such as when it is folded or constrained within a microcatheter. The microcatheter can be directed to the target site through a guide catheter or intermediate catheter using a guidewire or other commonly known technique in the art. The microcatheter can be forwarded across a clot and then withdrawn to expose the clot retrieval device and allow it to expand within the clot. The gaps in the non-circumferential first scaffolding section can allow at least a portion of the clot to exposed to the inner clot pinching element. Similarly, the radial force from the expansion of the fully circumferential second scaffolding section can displace portions of the clot through large outer cells so that the clot is engaged with the flow channel element. Expansion of the flow channel element can open a path to at least partially restore the flow of blood to recanalize the vessel.

To continue the method for removing the clot, the position of the clot retrieval device can be rigidly maintained while the outer catheter is advanced along the elongate shaft so that the collar of the outer catheter engages with the expandable element to pinch at least part of the clot in compression between the collar and the pinching element. Once the user feels resistance indicating that the clot has been pinched and grip is maintained, the outer catheter can be removed from the vessel in unison with the clot retrieval device and captured clot while maintaining the relative positions so the collar remains engaged with the expandable element of the clot retrieval device. The clot retrieval device and pinched clot can then be fully removed from the patient.

In many cases, after retrieving some or all of the occlusive clot, contrast media can be injected through the outer catheter to allow a more thorough assessment of the degree to which the vessel is patent. Additional passes with the thrombectomy device can be made if an obstruction remains in the vessel. Any remaining devices can then be removed from the patient once adequate recanalization of the target vessel is observed. The devices of the present disclosure provide a means to minimize the number of catheter advancements required to treat a patient, thereby reducing the likelihood of vessel damage and the associated risk of vessel dissection in cases where multiple passes are required.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with reference to the following description in conjunction with the accompanying drawings, where like reference numbers indicate elements which are functionally similar or identical. The drawings are not necessarily to scale, emphasis instead being placed upon illustrating principles of the invention. The figures depict one or more implementations of the inventive devices, by way of example only, not by way of limitation.

FIG. 1 is an isometric view of a clot retrieval device according to aspects of the present invention;

FIG. 2 shows another view of the clot retrieval device according to aspects of the present invention;

FIG. 4 shows another view of the outer cage of the clot retrieval device of FIG. 2 according to aspects of the present invention;

FIG. 5 illustrates the elongate inner body of the clot retrieval device of FIG. 2 according to aspects of the present invention;

FIG. 6 is an enlarged view of the strut structure of the clot pinching structure of the elongate inner body according to aspects of the present invention;

FIG. 7 illustrates an alternative elongate inner body of the clot retrieval device according to aspects of the present invention;

FIG. 8 is a view of another alternative elongate inner body of the clot retrieval device according to aspects of the present invention;

FIG. 9 shows a further alternative elongate inner body of the clot retrieval device according to aspects of the present invention;

FIG. 11b is a view showing the use of a clot retrieval device at a target location according to aspects of the present invention; FIG. 11c is a view showing the use of a clot retrieval device at a target location according to aspects of the present invention;

FIG. 11d continues the sequence of FIGS. 11a-c showing the interaction between the outer catheter and the pinching structure in the clot pinching configuration according to aspects of the present invention;

FIG. 11e continues the sequence of FIGS. 11a-c showing the dislodged clot being withdrawn from the vessel while being pinched in the clot pinching configuration according to aspects of the present invention; and FIG. 12 is a flow diagram outlining a method of use for the system according to aspects of the present invention.

FIG. 13 is a flow diagram outlining a method of use for the system according to aspects of the present invention.

DETAILED DESCRIPTION

Figure 3:
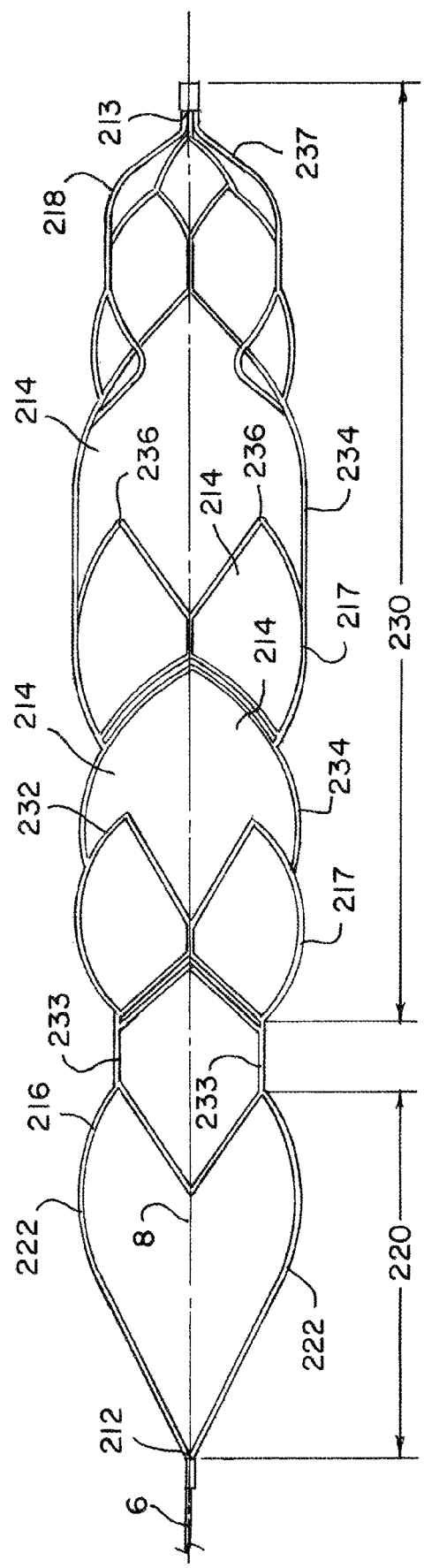
FIG. 3 shows the outer cage of the clot retrieval device of FIG. 2 according to aspects of the present invention.

The objective of the disclosed designs is to create a clot retrieval device capable of providing more effective and efficient removal of obstructions in the vasculature while maintaining a high level of deliverability and flexibility during procedures. The designs can have an outer expandable member within which runs an inner expandable member. The disclosed devices share a common theme of dual layer construction where the inner member has a clot pinching capture capability and minimal interference in this capability from the outer member. Both members can be directly or indirectly connected to an elongate shaft, and a distal net or scaffold configured at the distal end of the device can prevent the escape of clot fragments. This distal net may be appended to either the shaft, the inner or the outer members, or to multiple of these.

This dual layer construction is intended to allow a clot to enter through the large openings or gaps in the outer expandable member and reside in the reception space provided between the two expandable members. At least a portion of the inner member can have a denser scaffold than that of the outer member such that the clot is prevented from entering its lumen, creating a flow channel across the clot once the device is deployed across it.

Both the inner and outer expandable members are desirably made from a material capable of recovering its shape automatically once released from a highly strained delivery configuration. The material can be in many forms such as wire, strip, sheet, or tube. A suitable manufacturing process can be to laser cut a Nitinol tube and then heat set and electropolish the resultant structure to create a framework of struts and connecting elements. A range of designs are envisaged for each of these elements as described, and it is intended that any of these elements can be used in conjunction with any other element, although to avoid repetition they are not shown in every possible combination.

Specific examples of the present invention are now described in detail with reference to the Figures. While the description is in many cases in the context of mechanical thrombectomy treatments, the designs may be adapted for other procedures and in other body passageways as well.

Accessing the various vessels within the vasculature to reach a clot, whether they are coronary, pulmonary, or cerebral, involves well-known procedural steps and the use of a number of conventional, commercially available accessory products. These products, such as angiographic materials, rotating hemostasis valves, delivery access catheters, and guidewires are widely used in laboratory and medical procedures. When these or similar products are employed in conjunction with the disclosure of this invention in the description below, their function and exact constitution are not described in detail.

Referring to FIG. 1, a clot retrieval device 100 can have an elongate shaft 6 and an expandable structure configured at the distal end of the elongate shaft 6 having inner and outer members. The members can be an outer cage 210 and an elongate inner body 110 to capture a clot and facilitate the restoration of blood flow through the clot after the clot retrieval device 100 is deployed at a target site. The outer cage 210 can be a scaffolding structure with large cells through which the clot may pass and enter the reception space 9 defined by the annular region between the elongate inner body 110 and the outer cage. A fragment protection element 14 can be positioned approximate the tapered end 218 of the outer cage 210 near the distal end 4 of the device 100. The outer cage 210 and elongate inner body 110 can have a collapsed configuration for delivery within a microcatheter and an expanded configuration for clot retrieval, flow restoration and fragmentation protection.

The inner and outer members are preferably made of a super-elastic or pseudo-elastic material such as Nitinol or another such alloy with a high recoverable strain. Shaft 6 may be a tapered wire shaft, and may be made of stainless steel, MP35N, Nitinol or other material of a suitably high modulus and tensile strength. Shaft 6 and device 100 can have indicator bands or markers to indicate to the user when the distal end of the device is approaching the end of the microcatheter during insertion or mark the terminal ends of the device during a procedure. These indicator bands can be formed by printing, removing, or masking areas of the shaft for coating, or a radiopaque element visible under fluoroscopy, so that they are visually differentiated from the remainder of the shaft.

The shaft 6 may be coated with a material or have a polymeric jacket to reduce friction and thrombogenicity. The coating or jacket may consist of a polymer, a low friction lubricant such as silicon, or a hydrophilic/hydrophobic coating. This coating can also be applied to the outer cage 210 and elongate inner body 110.

A dual-layer, multi-diameter device 100 as shown in various figures throughout this disclosure has several advantages. The inner body 110 with a smaller radial size can embed firmly in a target clot for a secure grip with a steep opening angle, while the larger radial size of the outer cage 210 can remain in contact with and appose the vessel walls and protect against distal migration of the clot as the device is retracted proximally into progressively larger diameter vessels.

A top view of the compound device 100 with dual inner and outer expandable members of FIG. 1 is illustrated in FIG. 2. The inner body 110 and outer cage 210 can both be monolithic structures, where the outer cage is configured to substantially encapsulate the inner body. The cells of the outer cage 210 serve as inlets for the clot and allow the outer cage, when retracted, to apply a force to the clot in a direction substantially parallel to the direction in which the clot is to be pulled from the vessel (i.e., substantially parallel to the longitudinal axis 8). This means that the outward radial force applied to the vasculature can be kept to a minimum. By configuring the outer cage 210 so as to encourage a clot to traverse to the reception space 9 the device can more effectively disengage clot from the wall of the vessel. The outer cage 210 can also have an enclosed distal end 218 defining a surface configured to work with the fragment protection element 14 as a clot fragment barrier surface.

The elongate inner body can have multiple regions to provide both a strong grip on a clot and a strong opening force to create a lumen to restore flow on deployment. The elongate inner body 110 can have a proximal clot pinching section 120 which can provide a strong grip on the clot for the critical initial step of disengaging the clot from the vessel, enabling the outer cage 210 to be configured with a low radial force.

A distal section of the elongate inner body 110 can be a porous inner channel 130 configured to create a flow lumen through at least a portion of the clot. This flow lumen can reduce the pressure gradient across the clot, making it easier to dislodge and remove. The porous inner channel 130 can be a tubular shape and have a diameter when expanded that may be tailored so as to reduce the risk of a reperfusion injury. The restricted blood flow through the lumen can ensure that the pressure applied to blood vessels immediately after flow restoration is lower than normal thereby reducing the risk of bleeding in the vascular bed. Full perfusion can be subsequently restored by removing the device and the captured clot.

The outer cage member 210 can be a plurality of struts forming expandable bodies configured to self-expand upon release from a restraining sheath (such as a microcatheter) to a diameter larger than the radial size of the inner body 110, as shown in FIG. 3. Proximal expandable bodies 216 can be disposed around the clot gripping or pinching section 120 of the inner body 110 and distal expandable bodies 217 disposed around the porous inner channel 130. Proximally, the outer cage 210 can have support arms 222 joined at a proximal junction 212 to the shaft 6 and flare radially to form a proximal expandable body 216. The support arms 222 may have a tapered profile as shown to ensure a gradual stiffness transition from the shaft 6 to the clot-engaging expandable bodies. Support arms 222 can be oriented to form a network of closed cells at discrete positions around the longitudinal axis 8 of the device 100 so that there are large circumferential gaps between adjacent arms. For example, two sets of arms 222 can be largely diametrically opposed to each other by approximately 180 degrees as shown, or three sets of arms can be spaced 120 degrees apart.

The proximal portion of the outer cage 210 can have expandable bodies 216 with cells which are not completely circumferential around the device. providing a level of scaffolding that is less than that of the distal expandable bodies 217. Portions of a clot can pass into the gaps between the cells and support arms 222 of the proximal expandable bodies 216 so they are engaged by clot pinching structure 120. Having cells in the proximal expandable bodies 216 which are not completely circumferential can result in a lower surface contact area and a radial force which allows the clot to more easily protrude into the gaps in this section of the device. When the device is withdrawn into an outer catheter, the clot pinching structure 120 can maintain a secure grip on the clot without interfering impingement from the struts of the arms 222 of the outer cage 210. Support arms 222 can also have bends or crowns which would bias movement away from, or at least not in the same direction as, the clot pinching element so that the support arms do not shear portions of the clot when the proximal portion of the device is partially constrained by an outer catheter.

The proximal expandable body or bodies 216 can be connected to the most proximal body of the distal expandable bodies 217 by coupling struts 233. In one example these coupling struts 233 can be generally straight struts running parallel to the central longitudinal axis 8 of the device. In other examples the coupling struts 233 may have a plurality of struts configured in one or more cells or may have curved or spiral arms. The regions between adjacent expandable bodies 216, 217 can form inlets 214 through which the clot or portions of the clot may pass and enter the reception space 9 between the elongate inner body 110 and the outer cage 210.

The distal-most portion of the outer cage 210 can have a tapered end 218 which slims down radially in a substantially conical profile to a distal junction 213. The tapering and convergence of struts at the tapered end 218 reduces the pore size of the openings between struts to create a fragment capture zone. These struts can be end crown struts 237 connected to the distal-most distal expandable body 217 via connecting struts 234, as shown in FIG. 3. The end crowns 237 can be convexly bulged or flared so the end of the outer cage 210 is rendered atraumatic to the vessels in which it is used. The struts making the bulge or flare might not be parallel to those of the adjacent portions of the outer cage, forming a joint or hinge through which the tapered end 218 can bend or flex about the distal expandable bodies 217. The junction 213 can be a twisted or coiled collection of struts of fibers which can have, or be given, radiopaque properties to mark the terminal end of the device 100 during a procedure.

Distal expandable bodies 217 can in turn be connected by one or more connecting arms 234, which can extend from a proximal junction 239 to a distal junction 240, as seen in the side view of the outer cage 210 in FIG. 4. The connecting arms 234 can be generally straight and run parallel to the longitudinal axis 8 of the device 100. In other cases, the connecting arms may be a plurality of struts configured in one or more cells or can have a curved or spiral profile. The region between the distal expandable bodies 217 can define inlets 214 through which a clot may pass and enter the reception space 9. The connecting arms 234 between the distal expandable members 217 may be substantially aligned with the coupling struts 233 between the proximal and distal expandable bodies 216, 217 to align the neutral axis of the bodies during bending.

The proximal and distal expandable bodies 216, 217 of the outer cage 210 can have a series of interconnected struts to form the closed cells, with certain struts such as crown strut 232 terminating in crowns or distal apices 236 with no distal connecting elements to any adjacent closed cells, and other body struts such as 242 terminating in body junction points 244. The distal apices 236 can be offset from the longitudinal axis 8 of the device 100 and can be close to the cylindrical plane defined by the outer cage 210 when expanded. The crown struts 232 which join at a distal apex 236 can be broadly curved in order to maximize the offset and spacing between apices in order to achieve a desirable balance between clot scaffolding and device flexibility. Having the free apices 236 with no distal connections at some junctions can provide greater bending flexibility for the device. This is because, in addition to the flexing of the struts forming each cell, the apices themselves can flex to accommodate bends in the vasculature and have some capacity to react to clot forces.

The outer cage 210 can expand and contact the vessel wall as the microcatheter is retracted during device deployment. The contact provides stability to the device 100 and minimizes twisting as the inner elongate body 110 and any spiral portions of the pinching section 120 is unsheathed in the vessel. This facilitates uniform deployment and expansion of the device 100 in the obstruction or clot.

Expansion of the outer cage 210 can cause compression and/or displacement of the clot during the expansion, depending on the level of scaffolding support provided by the struts. When an expandable body provides a high level of scaffolding, the clot can be compressed. Alternately, when an expandable body provides an escape path or opening the expanding body will urge the clot towards the opening. The clot itself can have many degrees of freedom and can move in a variety of different directions. By providing an outer cage 210 whose length is substantially as long as the length of the occlusive clot or longer, many of the degrees of movement freedom available to the clot are removed. Inlet openings 214 are provided in the outer cage 210 to guide the primary movement freedom available to the clot and so the expansion of the outer cage urges the clot into the reception space 9. This allows the clot to be retrieved without being excessively compressed. This is advantageous because compression of the clot can cause it to dehydrate, which in turn increases the frictional properties and stiffness, which makes the clot more difficult to disengage and remove from the vessel. This compression can be avoided if the clot easily migrates inward through the cells or the gaps in the proximal portion of the outer cage as the outer cage expands outward towards the vessel wall.

Another advantage of using self-expanding bodies is that because of the volumetric properties and stiffness of a target clot, resistance can cause the device 100 to initially expand to only a fraction of its freely expanded diameter when deployed across the clot. This gives the outer cage 210 the capacity to further expand to a larger diameter while being retracted so that it can remain in contact with vessel walls as it is retracted into progressively larger and more proximal vessels.

FIG. 5 shows the inner elongate body 110 of the device 100 from FIG. 2. The clot engaging pinching section 120 and porous inner channel 130 can be formed integrally from a single strip or tube of a shape memory material such as Nitinol which is then laser cut to form the strut pattern. Alternately, they can be formed independently and later attached to allow both members to take on varied shapes. The inner body 110 can also have a proximal joint or transition between the proximal end 121 of the pinch section 120 and an elongate shaft 6 on which the device is mounted.

The elongate inner body 110 can be configured to expand to a lesser diameter than that of the smallest vessel in which it is intended to be used. When the inner body is non-tapered, this diameter is typically less than 50% that of the expanded outer cage diameter and in some cases may be as low as 20% or less of the outer cage diameter. This allows portions of the inner body can be constructed with a very small volume of material, as it is only required to expand to a fraction of the diameter of the outer cage and can thus be highly flexible in both the collapsed and expanded states. This flexibility can advantageously allow the inner body to be displaced in one direction by one portion of the clot and another direction by another portion of the clot.

The clot pinching section 120 can be an engaging element in the more proximal region of the inner elongate body 110 of the device 100. The pinching section 120 is intended to facilitate clot retrieval by expanding between the clot and the vessel wall in such a way as to engage with a clot over a significant surface area and do so with minimal compression of the clot. The overall clot compression is minimized because the section can be constructed to have rings of high compression with deep strut embedding interspersed with areas of minimal clot compression and low radial force. A portion of a clot can protrude into the area of low compression and be pinched between the tip of a catheter and the struts of the device. The pinch is achieved by forwarding a microcatheter or outer catheter over the proximal end 121 of the pinching section 120 until a portion of clot is compressed between the tip of the catheter and a crown or strut of the pinching section. This pinch facilitates removal of the clot as it increases the grip of the device on the clot, particularly for fibrin rich clots. It may also elongate the clot, thereby reducing the dislodgement force by pulling the clot away from the vessel wall during the dislodgement process. Retention of the clot during can be improved during retraction to the microcatheter or outer catheter by controlling the proximal end of the clot and preventing it from snagging on a side branch vessel.

Distal of the clot pinching section 120, the inner channel 130 can be generally tubular, planar, or some other shape, with a luminal structure being smaller in diameter than the surrounding portions of the outer cage 210. In one example, the distal inner channel 130 can transition from the distal end 122 of the clot pinching section to form a barrel shape so that this section is a smaller or larger radial size than that of the proximal pinch section 120 in the illustrated expanded configuration. This allows a flow channel to be created across very long clots without overly compressing the clot or engaging the inner channel 130 with the vessel wall. The inner channel 130 can be formed monolithically with the pinching section or can be formed separately and connected through a collar or other mechanical joint. In other cases, the inner channel 130 may have a non-cylindrical cross-section, may be non-uniform in diameter, and may have tailored strut patterns to provide regions of differing radial force or flexibility.

In another example, the shape can be substantially tubular and have a plurality of struts converging away from and towards the axis 8 of the device in intervals as shown in FIG. 5, the struts forming cells 132 configured to engage with and define a flow lumen through the clot in its expanded state. When expanded, the cells 132 can interpenetrate the clot and give additional grip to assist in the initial dislodgement of the clot while also scaffolding the flow lumen through the clot to prevent the liberation of fragments.

The distal end 136 of the inner channel 130 can transition to or be connected with a tether or shaft to a fragment protection structure 14. The fragment protection structure 14 can be a plurality of struts configured in a volumetric pattern, in a weave or entangled mesh filter, or in a basket-like or conical shape to impede or collect fragments from travelling distal of the device. The structure 14 can also be a bundle of fibers in a spherical or similar shape, and in the expanded state at least a portion of the fragment protection structure has a radial size larger than the flow channel 130 and pinching section 120 and can be similar in size to the diameter of the target blood vessel. The distal end of the fragment protection element 14 can have a radiopaque coil element 16, which can be laser cut from the same tubing used in the construction of the inner channel 130 during processing.

The inner elongate body 110 and outer cage 210 can be joined proximally at the shaft 6 and also distally during assembly so as to minimize tension between the members during use. The struts of the clot pinching segment 120, the inner channel 130, or both, can lengthen and shorten so that the lengths of the inner body and outer cage are substantially the same when loaded in a microcatheter and when freely expanded at the target site. The closed cells of the inner body and outer cage, along the coil element 16, can allow the device to accommodate minor length differentials through stretching without the application of significant tensile or compressive forces to the joints. Length differentials can occur when, for example, the device is expanded, collapsed, or deployed in a small vessel.

An enlarged and magnified view of the clot pinching section 120 of the inner elongate body 110 of FIG. 5 is shown in FIG. 6. Alternative ring segments 145 can be formed by overlapping struts and form intermediate crowns 147 at local apices. Section of low density fluting 146 can extend between and be bounded by consecutive ring segments 145, where longitudinally extending bridge struts exert a lower level of scaffolding and reduced radial force compared to that generated by the ring segments 145. The overlapping of the struts as the pinching section 120 expands or contracts can allow each ring segment 145 to twist relative to its adjacent rings, but where each twist can counterbalance the next so that minimal overall twisting occurs in the pinching section at the distal end 122 relative to the proximal end 121. Minimal twisting helps to ensure that the grip on a pinched clot is not lost.

The longitudinal length of the bridge struts in the low density fluting 146 between the ring segments 145 can vary. When used in the middle cerebral artery, for example, the longitudinal spacing can be approximately 3-6 mm. This spacing allows the clot to protrude between the struts where it engages the pinching section in the expanded deployed configuration. The total length and/or number of ring segments 145 and fluting sections 146 can be optimized for the expected length and density for optimum embedding in the clot. The bridge struts 144 between the ring segments 145 can be straight and parallel with the axis 8 of the device for better pushability to ensure the device can be delivered through tortuous anatomy.

Struts in the pinching section 120 can also have one or more bends 148 at various axial positions along their length. The "dog-leg" type shape created by these bends 148 in the struts 144 can be repeated around the circumference or radial direction of the section to form cells. The angle formed by the bends 148 or the length of the struts 144 can be varied in places, or different struts in the pattern can also have different widths so that various segments can have higher expansion force for improved engagement with the clot in the expanded deployed configuration. This structure can be produced by laser cutting Nitinol stock and heat-setting the shape so that it assumes the desired profile when expanded.

Another example of an inner elongate body 110 which has a proximal engaging element configured as a clot engaging pinching section 120 and a distal inner channel 130 is illustrated in FIG. 7. When fully expanded, the pinching section 120 can have the same or different radial size than the inner channel 130, but the two structures can be formed monolithically so there is not a significant stiffness transition at the distal end 122 of the pinching section. A fragment protection element 14 can be formed or otherwise attached to the distal end 136 of the inner channel 130 and be configured to transition to an expanded radial size greater than both the clot pinching section 120 and inner channel when the device 100 is deployed across a clot.

The pinching section 120 can have more densely spaced ring segments 145 along portions of its length as compared to that in FIG. 5. As discussed, this segment 120 can have rings 145 of struts and areas of low radial force and strut density 146. Having adjacent ring segments 145 spaced close together at certain axial locations of the pinching section 120 can increase the effect of the pinch between rings in the clot pinching configuration as a microcatheter or outer catheter is advanced.

During retraction, the pinch of a fibrin rich clot may be lost, or the clot may contain red blood cell rich 'soft' segments which are not fully gripped on the proximal pinch section 120. In these scenarios, the struts of the distal porous inner channel 130 can provide engagement with the clot and retrieve it through the increased diameter vessels, past the bends and branches to the microcatheter or outer catheter. Further, the expanded cells and/or struts of the fragment protection element 14 engage with any liberated fragments or ungripped clot sections with minimal shear.

Referring to FIG. 8, there is illustrated another inner elongate body 110 which has some features which are similar to other devices described above. The inner elongate body 110 can be attached proximally to a shaft 6. This connection can be a collar or some other axial constraint which allows at least partial relative rotation between the outer cage 210 and the inner body. Radiopaque markers (not shown) can also be used at this location to mark the proximal terminating point for the expandable portion of the device 100 during a procedure.

The inner body 110 can have a proximal clot engaging element 120 and a more distal tubular inner channel 130. A three-dimensional mesh-like structure or basket can be formed from wire or fiber into a fragment protection element 14, which is retained at the distal end 136 of the distal inner channel 130 and within the outer cage 210. The wire or fibers may be randomly curled and/or twisted to occupy the space within the structure, or they may be shaped into a specific pattern.

The clot engaging element 120 can have struts forming a plurality of adjacent segments 152, where differing shapes of the adjacent segments results in the radial force generated by successive adjacent segments being unequal. Some struts can have bends 148 (such as those seen in FIG. 6) so that adjacent struts 144 can compress the clot as the clot engaging element is transitioned from the expanded deployed configuration to the partially constrained clot pinching configuration. Struts in portions of the adjacent segments 152 can overlap at angles to the longitudinal axis 8 of the device so they can slide in different directions relative to each other when positioned in or moving through bends in the vasculature. Additionally, portions of adjacent segments 152 can have features which bias collapse along certain planes or change lengths in the axial or radial direction. The differences in strut length ensure that the radial force applied to a clot by the pinch section 120 varies to achieve good grip on the clot while facilitating clot retrieval in association with a microcatheter or outer catheter.

In another example of the device 100 shown in FIG. 9, the strut pattern of the clot pinching section 120 of the inner elongate member 110 can be formed by laser cutting a largely flat, two-dimensional sheet and wrapping the resultant flat pattern around a cylindrical mandrel prior to heat setting. The centerline of the device can then form a helical or spiral pattern around the longitudinal axis 8, similar to the process of wrapping a ribbon around a cylinder. At the proximal end the clot pinching structure 120 can be connected to a shaft 6. The inner channel 130 connected at the distal end 122 of the clot pinching section 120 can also be a flat pattern, have a curved or profiled cross section, or be a generally tubular shape as shown in other disclosed examples.

When deployed across a clot, portions of the clot can migrate through the inlets 214 and cells of the expandable bodies 216, 217 of the outer cage 210, or the spaces between expandable bodies, and into the reception space 9 or the device. Here, the clot can protrude into areas of low strut density and also into the central lumen of the helical spiral pattern of the clot pinching structure 120. The gaps and lower scaffolding of the proximal expandable bodies 216 facilitate ingress to the spiral of the clot pinching structure 120. When the device 100 is subsequently retracted, this spiral can improve grip and dislodgement performance and facilitate the clot pinching action when an outer catheter is forwarded distally to transition the device from the expanded deployed configuration to the partially constrained clot pinching configuration. Such an effect can also be increased if the clot pinching structure 120 of the device 100 was constructed from two or more helical spiral components.

A helical spiral shape can also allow portions of the clot pinching structure 120 to elongate under tension, stretching parts of the clot during dislodgement. The proximal end of the clot can be pinched and constrained on the clot pinching structure 120 while the distal end of the clot can be positioned on the inner channel 130 to embed and open a flow channel. If the distal end of the clot remains stuck in the vessel, the inner channel 130 and outer cage 210 can remain static while the clot pinching section 120 expands in some sections and contracts in others in response to clot forces. This action can help peel the clot from the vessel wall and reduce the dislodgement force during the procedure.

A fragment protection element 14 can be connected by a tether or shaft 134 to the distal end 136 of the inner channel 130. The protection element 14 can be a volumetric pattern which expands to a larger radial size than the radial size at any point along the cross section of the elongate inner body 110. The shape of the element can be a conical basket as shown or a mesh element or fibrous bundle occupying sufficient space to impede the distal passage of clot or thrombus fragments.

Figure 10:
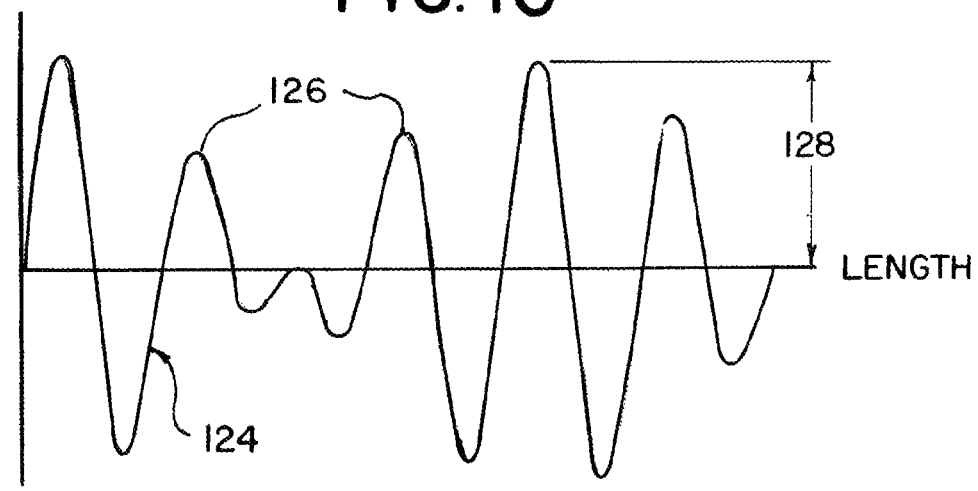
FIG. 10 is an example plot of the radial force exerted by axial position along the clot pinching structure according to aspects of the present invention.

The exact shape and configuration of the strut network and adjacent segments 152 of the clot pinching element 120 will determine the radial force extorted at different axial positions along the structure when the element is in the expanded deployed configuration and clot pinching configuration. The force can vary, for example, in a generally sinusoidal waveform pattern 124 with locally varying peaks 126 determining the amplitude 128 of force at that position. A sample plot of radial force as a function of axial position along the clot engaging element 120 is shown to illustrate this concept in FIG. 10. The amplitude 128 can repeat at a patterned distance so that it is relatively equal along the length of the engaging element 120, or it can decrease along the length so that the force is lower at the distal end 122 and higher at the proximal end 121 where with initial grip of the pinch allows for disengagement of the clot. The plot shows how, for example, the ring segments 145 which embed in the clot can have a higher radial force than the low-density fluting segments 146 between the rings. The effectiveness of areas of increased radial force can be increased by maximizing the angle of the struts with respect to the longitudinal axis of the vessel, which can allow the ring segments 145 to grip, rather than slide past, the clot. Having these regions of differing radial force allows the device 100 to maintain a grip on the clot in the area of the peaks 126 while exerting much less compression on the clot between peaks, which helps to minimize the overall force required to retract the clot.

As a microcatheter or outer catheter is advanced to increase the pinch on a clot, the user may feel the pinching as resistance and stop advancement of the catheter, or alternately may advance a fixed distance over the proximal end 121 of the engaging element 120 and the more proximal expandable bodies 216 of the outer cage 210. The lower level of scaffolding in the proximal expandable bodies 216 of the outer cage 210 allows the relative tension between the engaging element 120 and catheter to be maintained so that the pinch between the engaging element and the catheter does not deteriorate during retraction of the clot.

Figure 11A:
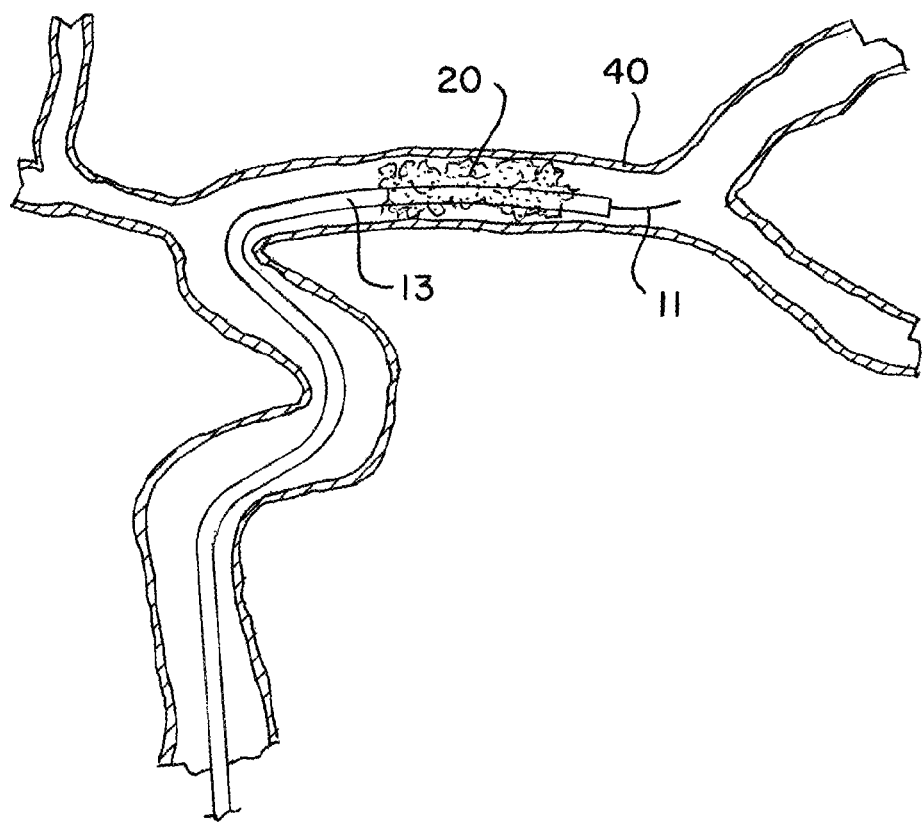
FIG. 11a is a view showing the use of a clot retrieval device at a target location according to aspects of the present invention.

FIGS. 11a-11e and the flow diagrams of FIG. 12 and FIG. 13 show a method of use for the disclosed designs. A guidewire 11 and microcatheter 13 are inserted and guided through the vasculature 40 and advanced across the obstructive clot 20 using conventionally known techniques. When the microcatheter 13 is positioned distal to the occlusive clot 40, the guidewire 11 can be removed from the vessel 40 to allow the clot retrieval device 100 be advanced through the microcatheter. The device 100 is advanced in a collapsed configuration until the distal tip of the device reaches the distal end of the microcatheter. The microcatheter 13 can be retracted while the position of device 100 is maintained using the shaft 6 to deploy the clot retrieval device across the clot 20, preferably in a manner so that the distal end of the device is positioned distal of the clot, as shown in FIG. 11b. The device 100 expands so that the outer cage 210 can engage with the occlusive clot 20 and allow the clot to pass radially inward. The clot pinching section 120 and porous inner channel 130 can expand to embed with the clot and provide a flow channel to restore blood flow in a controlled manner. The device 100 may be allowed to incubate for a period of time within the clot 20 if desired, as the controlled flow that has been restored through the inner channel 130 is stabilized.

FIG. 11c illustrates the clot 20 engaged with the device during retrieval into the microcatheter 13. Advancement of the catheter causes the collar 12 to compress the clot 20 between the crowns 147 of the ring segments 145 and the bridging struts 144 of the low-density fluting segments 146, as shown in FIG. 11d. Depending on conditions, the pinching engagement can also be effected with an intermediate or other outer catheter. The clot can be partially located in the inlet openings 214 of the device and also partially located in the reception space 9 defined by the region between the inner body 110 and outer cage 210. Clot fragments can be trapped in the distal closed tapered end 218 of the outer cage 210 and the fragment protection element 14 to prevent the fragments from being released in the blood flow. Flow occlusion, aspiration and other standard techniques may be used during this process.

The relative tension between the device and the microcatheter can be maintained by the user during dislodgment and retraction to ensure the pinch on the clot is maintained, as in FIG. 11e. While the use of a microcatheter or intermediate catheter to pinch the clot is described as giving additional benefits when used with this invention, all the embodiments described herein can also be used to dislodge and retrieve clots without the use of catheter pinching if required. The distal closed end of the outer cage 210 and the expanded fragment protection element 14 of the device 100 prevents trapped clot fragments from being released in the blood flow.

FIG. 12 and FIG. 13 diagram method steps for performing a thrombectomy procedure with such a device. The method steps can be implemented by any of the example devices or suitable alternative described herein and known to one of ordinary skill in the art. The method can have some or all of the steps described, and in many cases, steps can be performed in a different order than as disclosed below.

Referring to a method 1200 outlined in FIG. 12, step 1210 can involve providing an outer catheter which can have a tubular body and a collar at its distal end. Depending on circumstances, the outer catheter can be a microcatheter, intermediate catheter, or any other suitable sheath known to those in the art with a diameter appropriate for effecting a pinch on the device as previously described.

Step 1220 can provide for a clot retrieval device having a collapsed delivery configuration, an expanded deployed configuration, and an expandable element. A proximal shaft can be used to manipulate the device during a procedure. The expandable element can have an inner body and an outer body expandable to a greater radial extent than the inner body. The inner body can have a proximal pinching element and a distal flow channel element. The outer body can have a non-circumferential first scaffolding section disposed around the pinching element and a fully circumferential second scaffolding section around the flow channel element and connected distal of the first scaffolding section. The non-circumferential first scaffolding segment can allow for portions of the clot in the vicinity can easily pass inward through gaps in the outer body to engage with the proximal pinching element of the inner body.

Step 1230 can involve delivering the clot retrieval device in the collapsed delivery configuration to the occluded vessel through a microcatheter. In the case of an intracranial occlusion a variety of access routes are possible, including a direct stick into the carotid artery, a brachial approach, or a femoral access. Once access has been gained to the arterial system using conventional and well understood techniques, a guide catheter or long sheath (not shown as part of FIGS. 11a-e) is typically placed as close to the occlusive clot as practical. For example, in the case of a middle cerebral artery occlusion, the guide catheter might be placed in the internal carotid artery proximal of the carotid siphon. A microcatheter can then be advanced across a clot with or without the aid of a guidewire. Once the microcatheter tip has been advanced across and distal of the clot, the guidewire, if used, can be removed and the clot retrieval device is advanced through the microcatheter until it reaches the distal end.

The microcatheter can then be retracted allowing the clot retrieval device to expand within and either side of the clot in step 1240. This step can further involve the scaffolding regions of the outer body expanding within the clot to apply a compressive force to urge the clot to flow through the inlet cells and into the space between the inner and outer bodies. As the outer body is deployed to the expanded deployed configuration, at least a portion of the clot can pass radially through circumferential gaps in the non-circumferential first scaffolding section and into contact with at least a portion of the pinching element. Because of the large cell openings in the outer body, and the gaps in the non-circumferential first scaffolding section, clot compression can be controlled and minimized. Minimizing compression on the clot reduces the forces applied radially outward to the vessel wall, which in turn reduces the frictional forces to be overcome when retracting the clot.

Continuing to FIG. 13, method 1300 can have a step 1310 of inhibiting migration of the clot into the flow channel element to allow a flow of blood through the flow channel element in the expanded deployed configuration. Because the device can be configured with a two-part long inner body, upon device deployment the expansion of the flow channel element can create a flow channel through the clot, restoring flow to the vascular bed distal of the clot and reducing the pressure gradient across the clot. This reduction in pressure gradient reduces the force required to disengage the clot from the vessel wall and retract it proximally. Additionally, a flow channel allows the device can be safely left in place for a dwell period prior to withdrawal. A dwell period allows the distal vascular bed to be gently perfused with fresh oxygenated blood rather than be exposed to a sudden transient spike in pressure and flow as would be the case if the clot were immediately removed or if the device were to compress the clot so much that a very large flow channel was created upon deployment.

While rigidly maintaining the position of the clot retrieval device, step 1320 can involve advancing the outer catheter along the elongate shaft so that the collar of the outer catheter engages with the expandable element to pinch in compression at least a portion of the clot with the pinching element. This can be done with the aid of aspiration through the outer and/or guide catheter to assist in retaining a firm grip on the clot and avoiding fragment loss. However, the disclosed designs grip the clot securely and houses the clot safely within a reception space, with the added benefit of having a distal fragment protection element and scaffolding region. The protection element may be spaced apart from the distal end of the inner member, so it is optimally positioned to trap any fragments released from the clot during retraction.

In step 1330, the outer catheter and the clot retrieval device are withdrawn in unison from the vessel while maintaining the engagement between the collar of the outer catheter and the expandable element. Along with aspiration, this engagement maintains the firm pinching grip on the clot as it is withdrawn through bends and successively larger vessel diameters.

In step 1340, the clot retrieval device and the pinched clot can be removed from the patient. The device may be rinsed in saline and gently cleaned before being reloaded into the microcatheter, if required. It can then be reintroduced into the vasculature to be redeployed in additional segments of an occlusive clot, or if further passes for complete recanalization are needed.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology. For clarity and conciseness, not all possible combinations have been listed, and such variants are often apparent to those of skill in the art and are intended to be within the scope of the claims which follow.

What is claimed is:

1. A method of treating a patient with a clot occluding a vessel, the method comprising the steps of:
providing an outer catheter comprising a tubular body and a collar at its distal end;
providing a clot retrieval device comprising a collapsed delivery configuration, an expanded deployed configuration, an elongate shaft, and an expandable element distal of the elongate shaft, the expandable element comprising:
an inner body comprising a proximal pinching element, the proximal pinching element comprising a plurality of adjacent segments having different shapes and being configured such that a radial force exerted by at least two adjacent segments of the plurality of adjacent segments having different sizes differs from each other, and an inner channel connected distal of the proximal pinching element; and
an outer body extending along a longitudinal axis comprising a non-circumferential first scaffolding section and a fully circumferential second scaffolding section pivotably connected distal of the first scaffolding section;
delivering the clot retrieval device in the collapsed configuration to the occluded vessel through a microcatheter;
deploying the clot retrieval device so that at least a portion of the clot passes radially through circumferential gaps in the non-circumferential first scaffolding section and into contact with at least a portion of the proximal pinching element;
while rigidly maintaining the position of the clot retrieval device, advancing the outer catheter along the elongate shaft so that the collar of the outer catheter engages with the expandable element to pinch in compression the at least a portion of the clot with the at least a portion of the proximal pinching element;
withdrawing in unison the outer catheter and the clot retrieval device from the vessel while maintaining the engagement between the collar and the expandable element; and
removing the clot retrieval device and the at least a portion of the pinched clot from the patient,
wherein the non-circumferential first scaffolding section comprises one or more proximal expandable bodies, each proximal expandable body of the one or more proximal expandable bodies comprising a plurality of closed cells that are non-circumferentially located around the non-circumferential first scaffolding section.

2. The method of claim 1, further comprising inhibiting migration of the at least a portion of the clot into the inner channel to allow a flow of blood through the inner channel in the expanded deployed configuration.

3. The method of claim 1, wherein the non-circumferential first scaffolding section and the fully circumferential second scaffolding section of the outer body expand within the at least a portion of the clot to apply a compressive force to urge the at least a portion of the clot to flow through inlet cells and into a space between the inner body and the outer body.

4. The method of claim 1, wherein the non-circumferential first scaffolding section further comprises one or more coupling struts, wherein each coupling strut of the one or more coupling struts couples a proximal expandable body of the one or more proximal expandable bodies to the fully circumferential second scaffolding section.

5. The method of claim 1, wherein the outer body is expandable to a radial extent greater than the inner body to define a reception space between the outer body and the inner body.

6. The method of claim 1, wherein one or both of the proximal pinching element and the inner channel expand to embed within the at least a portion of the clot.

7. The method of claim 1, wherein the non-circumferential closed cells of the first non-circumferential scaffolding section comprise one or more support arms, the one or more support arms spaced around the longitudinal axis to form large circumferential gaps between adjacent one or more arms.

8. The method of claim 1, wherein a fragment protection structure of the inner body is located proximal of a closed distal junction of the outer body.

9. The method of claim 1, wherein the first non-circumferential scaffolding section further comprises one or more coupling struts each coupling a proximal expandable body of the one or more proximal expandable bodies to the second fully circumferential scaffolding section.

10. The method of claim 1, wherein each proximal expandable body of the first non-circumferential scaffolding section and each distal expandable body of the fully circumferential second scaffolding section comprise at least one distal apex free from connection to an adjacent closed cell.

11. The method of claim 1, wherein the proximal pinching element comprises:
a plurality of clot-receiving cells, and
each cell comprises struts extending between crowns, the struts being configured to pinch the at least a portion of the clot located in the cell as the proximal pinching element is moved from the expanded deployed configuration to the at least partially constrained clot pinching configuration.

12. The method of claim 1, wherein adjacent struts of the proximal pinching element comprise at least one bend, the at least one bend being configured so that the adjacent struts compress the at least a portion of the clot as the proximal pinching element is moved to an at least partially constrained clot pinching configuration.

13. The method of claim 1, wherein the fully circumferential second scaffolding section comprises one or more distal expandable bodies comprising a plurality of fully circumferential closed cells distal of the non-circumferential first scaffolding section, the inner channel extending inside the fully circumferential second scaffolding section.

14. The method of claim 13, wherein struts of the inner channel define inner body closed cells, and wherein the closed cells of the non-circumferential first scaffolding section and the closed cells of the second fully circumferential scaffolding section of the outer body are larger than the inner body closed cells.

15. The method of claim 13, wherein the proximal expandable bodies of the non-circumferential first scaffolding section and the distal expandable bodies of the second fully circumferential scaffolding section are hingedly connected to each other.

16. The method of claim 1, wherein the radial force varies in a generally sinusoidal waveform pattern along a length of the proximal pinching element.

17. The method of claim 16, wherein an amplitude of the waveform pattern is generally equal along the length of the proximal pinching element.

18. The method of claim 16, wherein an amplitude of the waveform pattern decreases along the length of the proximal pinching element, being higher at a proximal end of the proximal pinching element and lower at a distal end of the proximal pinching element.

19. The method of claim 16, wherein the clot retrieval device has a longitudinal axis extending through the proximal pinching element and the inner channel, and wherein struts of the proximal pinching element form a planar pattern disposed in a spiral configuration around the longitudinal axis.

* * * * *